United States Patent
Seipel et al.

(10) Patent No.: US 6,835,701 B2
(45) Date of Patent: Dec. 28, 2004

(54) CLEANING TOWELS FOR HAIR CARE

(75) Inventors: Werner Seipel, Hilden (DE); Hermann Hensen, Haan (DE); Dagmar Goebels, Voerde (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 10/473,855

(22) PCT Filed: Mar. 30, 2002

(86) PCT No.: PCT/EP02/03561

§ 371 (c)(1),
(2), (4) Date: Oct. 2, 2003

(87) PCT Pub. No.: WO02/080865

PCT Pub. Date: Oct. 17, 2002

(65) Prior Publication Data

US 2004/0102352 A1 May 27, 2004

(30) Foreign Application Priority Data

Apr. 7, 2001 (DE) .......................... 101 17 500

(51) Int. Cl.$^7$ .............................. C11D 1/72; C11D 3/22; C11D 3/37; C11D 17/00
(52) U.S. Cl. ...................... 510/143; 510/295; 510/438; 510/470; 510/475; 424/70.13
(58) Field of Search ................................ 510/143, 295, 510/438, 470, 475; 424/70.13

(56) References Cited

U.S. PATENT DOCUMENTS 4,725,489 A * 2/1988 Jones et al. ................. 442/121
6,391,835 B1 * 5/2002 Gott et al. ................... 510/143

* cited by examiner

Primary Examiner—Brian P Mruk
(74) Attorney, Agent, or Firm—Aaron R. Ettelman

(57) ABSTRACT

A cleaning cloth impregnated with a composition comprising: (a) a fibrous web; (b) an alkyl or alkenyl oligoglycoside; (c) a mixture comprising an alcohol polyglycol ether, a hydroxy mixed ether, or a combination thereof are useful for cleansing hair.

11 Claims, No Drawings

CLEANING TOWELS FOR HAIR CARE

This invention relates generally to hair care and, more particularly, to the use of cleaning cloths impregnated with a special surfactant solution.

BACKGROUND OF THE INVENTION

Numerous patent applications describe cleaning cloths with a disinfecting effect, cf. WO 95/17175 or WO 98/55096. Various textiles are used as the carrier material for impregnation with cleaning solutions (WO 99/13861 and WO 01/08657). WO 99/66793 mentions active components which can be applied to cloths.

Besides cleaning, skin care is also being increasingly taken into consideration. For example, WO 95/35411 describes wet wipes impregnated with a lotion which, besides mineral oil, contains fatty acid esters, fatty alcohol ethoxylates and fatty alcohols. These wet wipes are mainly intended for use on the skin. Even where they mention use on the hair, the cited applications do not solve the problem of the hair fibers sticking together or the components remaining on the scalp which presupposes very high compatibility of the compounds.

Accordingly, a first problem addressed by the invention was to provide cleaning cloths for hair care using special highly compatible surfactants which would be simple, clean and quick to use and which would have a good cleaning effect. These surfactants would not cause hair fibers to stick together because the intention would be for the formulations to remain in the hair after application.

Another problem arises in the production of wet wipes. In order to impregnate it with the cleaning solution, the cloth or tissue paper is either sprayed with or immersed in the cleaning solution. In either case, foaming or inadequate wetting can lead to a reduction in throughput in production. Accordingly, another problem addressed by the present invention was to provide a surfactant solution which, by virtue of its viscosity and low foaming, would be rapidly absorbed into the cloths so that the surfactants could be thoroughly distributed throughout, thereby enabling wet wipes to be produced in a technically simple and hence inexpensive manner. However, if the cleaning cloths are intended to be dry and wetted with water before use, rapid evaporation of the solvent during production is desirable.

DESCRIPTION OF THE INVENTION

The present invention relates to the use of cleaning cloths distinguished by the fact that they are impregnated with a surfactant solution containing (a) alk(en)yl oligoglycosides,
(b) alcohol polyglycol ethers and/or
(c) hydroxy mixed ethers for the care and cleaning of hair.

It has been found that cleaning cloths containing surfactant mixtures of alk(en)yl oligoglycosides in combination with alcohol polyglycol ethers or hydroxy mixed ethers solve the complex problem stated above in excellent fashion. After application to hair, they show a distinct cleaning effect without leaving any feeling of stickiness behind. In addition, cleaning performance, hair volume and hair luster can be influenced through the choice of solvent. As a so-called leave-on formulation, the surfactant mixture applied is highly compatible so that there is no need for subsequent rinsing of the hair. Accordingly, simple and hygienic use for cleaning hair is even possible in cases where hair cannot be washed in the usual way as, for example, with bedridden patients or on journeys.

In addition, the applied surfactant solutions based on alk(en)yl oligoglycosides and alcohol polyglycol ethers and/or hydroxy mixed ethers have been found to be readily processable, low in viscosity and largely foam-free in production so that they are rapidly absorbed by the particular cloth. This effect is further enhanced by the use of an alcoholic/aqueous solvent.

Alkyl and/or Alkenyl Oligoglycosides

Alk(en)yl oligoglycosides are known nonionic surfactants which correspond to formula (I):

$$R^1O\text{---}[G]_p \quad (I)$$

where $R^1$ is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry. EP-A1 0301298 and WO 90/03977 are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred. The alkyl and/or alkenyl oligoglycosides may be used in quantities—based on the wet wipes—of 0.05 to 2 and preferably 0.5 to 1 % by weight and in quantities—based on the concentrates—of 30 to 80 and preferably 50 to 70% by weight, the ratio by weight of alcohol polyglycol ethers to glycoside being in the range from 10:90 to 90:10, preferably in the range from 25:75 to 75:25 and more particularly in the range from 40:60 to 60:40.

Alcohol Polyglycol Ethers

Alcohol polyglycol ethers are known nonionic surfactants which are normally obtained by addition of ethylene oxide and/or propylene oxide blockwise or in random distribution onto suitable primary alcohols or polyols. The polyglycol ethers normally correspond to formula (II):

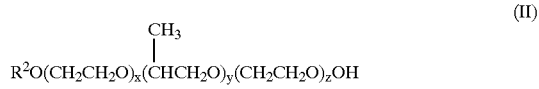

$$R^2O(CH_2CH_2O)_x(CHCH_2O)_y(CH_2CH_2O)_zOH \quad \text{with } CH_3 \text{ branch} \tag{II}$$

in which $R^2$ is a linear and/or branched alkyl and/or alkenyl group containing 6 to 22, preferably 8 to 18 and more particularly 10 to 12 carbon atoms, an ethylene glycol or glycerol unit, x and z independently of one another stand for 0 or numbers of 1 to 40 and y stands for numbers of 1 to 40. Accordingly, the polyglycol ethers compulsorily contain at least one propylene oxide unit. Typical examples are products of the addition of on average 1 to 40, preferably 5 to 30 and more particularly 8 to 15 mol ethylene oxide and/or 1 to 10 and preferably 2 to 5 mol propylene oxide onto fatty alcohols, oxoalcohols or Alfols such as, for example, caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof and also ethylene glycol or glycerol.

Hydroxy Mixed Ethers

Hydroxy mixed ethers (HMEs) are known nonionic surfactants with a nonsymmetrical ether structure and a content of polyalkylene glycols which are obtained, for example, by subjecting olefin epoxides to a ring opening reaction with fatty alcohol polyglycol ethers. Hydroxy mixed ethers typically correspond to general formula (III):

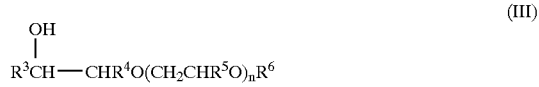

$$R^3CH-CHR^4O(CH_2CHR^5O)_nR^6 \quad \text{with OH} \tag{III}$$

in which $R^3$ is a linear or branched alkyl group containing 2 to 18 and preferably 10 to 16 carbon atoms, $R^4$ is hydrogen or a linear or branched alkyl group containing 2 to 18 carbon atoms, $R^5$ is hydrogen or methyl, $R^6$ is a linear or branched alkyl and/or alkenyl group containing 1 to 22 and preferably 18 to 18 carbon atoms and n is a number of 1 to 50, preferably 2 to 25 and more preferably 5 to 15 with the proviso that the total number of carbon atoms in the substituents $R^3$ and $R^4$ is at least 4, preferably 6 to 18 and more particularly 8 to 12. As the formula suggests, the HMEs may be ring opening products both of internal olefins ($R^4 \neq$ hydrogen) or terminal olefins ($R^4$=hydrogen), the latter being preferred for their more favorable performance properties and their easier production. Similarly, the polar part of the molecule may be a polyethylene or a polypropylene chain. Mixed chains of PE and PP units in statistical or block distribution are also suitable. Typical examples are ring opening products of 1,2-hexene epoxide, 2,3-hexene epoxide, 1,2-octene epoxide, 2,3-octene epoxide, 3,4-octene epoxide, 1,2-decene epoxide, 2,3-decene epoxide, 3,4-decene epoxide, 4,5-decene epoxide, 1,2-dodecene epoxide, 2,3-dodecene epoxide, 3,4-dodecene epoxide, 4,5-dodecene epoxide, 5,6-dodecene epoxide, 1,2-tetradecene epoxide, 2,3-tetradecene epoxide, 3,4-tetradecene epoxide, 4,5-tetradecene epoxide, 5,6-tetradecene epoxide, 6,7-tetradecene epoxide, 1,2-hexadecene epoxide, 2,3-hexadecene epoxide, 3,4-hexadecene epoxide, 4,5-hexadecene epoxide, 5,6-hexadecene epoxide, 6,7-hexadecene epoxide, 7,8-hexadecene epoxide, 1,2-octadecene epoxide, 2,3-octadecene epoxide, 3,4-octadecene epoxide, 4,5-octadecene epoxide, 5,6-octadecene epoxide, 6,7-octadecene epoxide, 7,8-octadecene epoxide and 8,9-octadecene epoxide and mixtures thereof with addition products of on average 1 to 50, preferably 2 to 25 and more particularly 5 to 15 mol ethylene oxide and/or 1 to 10, preferably 2 to 8 and more particularly 3 to 5 mol propylene oxide onto saturated and/or unsaturated primary alcohols containing 6 to 22 and preferably 12 to 18 carbon atoms, such as for example caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof.

Tissue Papers and Tissue Cloths for Cleaning Cloths

Tissue papers and cloths to which the present invention relates may have a single-ply or multi-ply structure. The papers generally have a weight per squate meter of 10 to 65 and preferably 15 to 30 g and a density of 0.6 $g/cm^3$ or less.

Besides paper-based tissues, corresponding tissue cloths made of fibers or fleeces are also suitable. Examples of natural fibers include silk, cellulose, keratin, wool, cotton, jute, linen, flax; examples of synthetic fibers include acetate, acrylate, cellulose ester, polyamide, polyester, polyolefin, polyvinyl alcohol, polyurethane fibers. It is preferred to use hydrophilic fibers, natural fibers, such as cotton cloth and cotton blends. Additive-hydrophilicized polyolefin fabrics are particularly preferred. Reaction products of 1 part polyethylene glycol with 2 parts $C_{10-12}$ fatty acids or derivatives thereof are used to hydrophilicize the polyolefin-containing fabrics.

The cloth may be in the form of a glove and, in that case, preferably has a multi-ply structure so that the inner fabric layer of the glove has a barrier function and protects the hand against contact with the formulation or with moisture.

Cleaning Solution and Solvents

The ratio by weight of dry cloth to applied cleaning solution should be 1:0.1 to 1:4 and is preferably from 1:0.5 to 1:3 and more preferably from 1:1 to 1:2. The solvent of the cleaning solution should consist of water or, preferably, water/alcohol mixtures. Isopropanol, propanol and ethanol are used as the alcohols. The cleaning solutions used for impregnation contain 0 to 95% by weight alcohol, preferably 3 to 70% by weight alcohol and more particularly 5 to 20% by weight alcohol. Where wet cleaning cloths are used, solubilization of the hair fat is influenced not only by the type and quantity of surfactants used, but also by the alcohol content so that the cleaning effect and the volume and luster of the cleaned hair can be controlled through the alcohol content. Even in the production of dry cleaning cloths which are wetted before use, the alcohol content of the solution used has a criticial influence because the drying rate and hence the production costs can be optimized.

Production Process

The process for the production of cleaning cloths is characterized in that a cloth is wetted with a surfactant solution containing (a) alk(en)yl oligoglycosides,
(b) alcohol polyglycolethers and/or (c) hydroxy mixed ethers and the solvent is then optionally removed by drying to a residual content of 0.1 to 3% by weight and preferably less than 0.1% by weight, based on the weight of the cleaning cloth. Wetting may be carried out by spraying the surfactant solution onto the cloth or by immersing the cloth in the surfactant solution. If the solvent is to be subsequently evaporated, the wetted cloths are exposed to an elevated temperature, to a warm air stream or to vacuum drying.

Commercial Applications

The present invention also relates to the use of cleaning cloths, characterized in that they are impregnated with a surfactant solution which typically has the following composition:

(a) 0.1 to 10% by weight, preferably 0.5 to 5% by weight and more particularly 1 to 3% by weight alk(en)yl oligoglycosides, (b) 0.01 to 5% by weight, preferably 0.1 to 3% by weight and more particularly 0.3 to 0.5% by weight alcohol polyglycol ethers and/or (c) 0.01 to 5% by weight, preferably 0.1 to 3% by weight and more particularly 0.3 to 0.5% by weight hydroxy mixed ethers, for the care and cleaning of hair.

The surfactant solutions used for impregnation may additionally contain mild surfactants, emulsifiers, consistency factors, thickeners, stabilizers, polymers, silicone compounds, lecithins, phospholipids, biogenic agents, UV protection factors, antioxidants, antidandruff agents, film formers, hydrotropes, solubilizers, preservatives, perfume oils, dyes and the like as further auxiliaries and additives.

Other Surfactants

Suitable surfactants are anionic, nonionic, cationic and/or amphoteric or zwitterionic surfactants which normally make up about 1 to 70, preferably 5 to 50 and more preferably 10 to 30% by weight of the impregnating solution. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are alkylphenol polyglycol ethers, fatty acid polyglycol esters, fatty acid amide polyglycol ethers, fatty amine polyglycol ethers, alkoxylated triglycerides, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow homolog distribution. Typical examples of cationic surfactants are quaternary ammonium compounds, such as dimethyldistearyl ammonium chloride for example, and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217. Typical examples of particularly suitable mild, i.e. particularly dermatologically safe, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, fatty acid glucamides, alkyl amidobetaines, amphoacetates and/or protein fatty acid condensates—the latter preferably based on wheat proteins.

Emulsifiers

Suitable other emulsifiers are, for example, nonionic surfactants from at least one of the following groups:

products of the addition of 2 to 30 mol ethylene oxide onto linear $C_{8-22}$ fatty alcohols, $C_{12-22}$ fatty acids, alkyl phenols containing 8 to 15 carbon atoms in the alkyl group and alkylamines containing 8 to 22 carbon atoms in the alkyl group;

products of the addition of 1 to 15 mol ethylene oxide onto castor oil and/or hydrogenated castor oil;

products of the addition of 15 to 60 mol ethylene oxide onto castor oil and/or hydrogenated castor oil;

partial esters of glycerol and/or sorbitan with unsaturated, linear or saturated, branched fatty acids containing 12 to 22 carbon atoms and/or hydroxycarboxylic acids containing 3 to 18 carbon atoms and addition products thereof onto 1 to 30 mol ethylene oxide;

partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and addition products thereof onto 1 to 30 mol ethylene oxide;

mixed esters of pentaerythritol, fatty acids, citric acid and fatty alcohol according to DE 1165574 PS and/or mixed esters of fatty acids containing 6 to 22 carbon atoms, methyl glucose and polyols, preferably glycerol or polyglycerol;

mono-, di- and trialkyl phosphates and mono-, di- and/or tri-PEG-alkyl phosphates and salts thereof;

wool wax alcohols;

polysiloxane/polyalkyl/polyether copolymers and corresponding derivatives;

block copolymers, for example Polyethylene Glycol-30 Dipolyhydroxystearate;

polymer emulsifiers, for example Pemulen types (TR-1, TR-2) from Goodrich;

polyalkylene glycols and
glycerol carbonate.

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol Esters

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic Emulsifiers

Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric and Cationic Emulsifiers

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Finally, other suitable emulsifiers are cationic surfactants, those of the esterquat type, preferably methyl-quaternized difatty acid triethanolamine ester salts, being particularly preferred.

Consistency Factors and Thickeners

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum, guar-guar, agar-agar, alginates and tyloses, carboxymethyl cellulose and hydroxyethyl and hydroxypropyl cellulose, also relatively high molecular weight polyethylene glycol monoesters and diesters of fatty acids, polyacrylates (for example Carbopols® and Pemulen types [Goodrich]; Synthalens® [Sigma]; Keltrol types [Kelco]; Sepigel types [Seppic]; Salcare types [Allied Colloids]), polyacrylamides, polymers, polyvinyl alcohol and polyvinyl pyrrolidone. Other consistency factors which have proved to be particularly effective are bentonites, for example Bentone® Gel VS-5PC (Rheox) which is a mixture of cyclopentasiloxane, Disteardimonium Hectorite and propylene carbonate. Other suitable consistency factors are surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Stabilizers

Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2252840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones. Other suitable polymers and thickeners can be found in Cosm. Toil., 108, 95 (1993).

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

UV Protection Factors and Antioxidants

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)camphor as described in EP 0693471 B1;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)1,3,5-triazine and Octyl Triazone as described in EP 0818450 A1 or Dioctyl Butamido Triazone (Uvasorb® HEB);

propane-1,3-diones such as, for example, 1-(4-tert.butylphenyl)-3-(4'-methoxyphenyl)-propane-1,3-dione;

ketotricyclo(5.2.1.0)decane derivatives as described in EP 0694521 B1.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789) or 1-phenyl-3-(4'-isopropylphenyl)-propane-1,3-dione and the enamine compounds described in DE 19712033 A1 (BASF). The UV-A and UV-B filters may of course also be used in the form of mixtures. Particularly favorable combinations consist of the derivatives of benzoyl methane, for example 4-tert.butyl-4'-methoxydibenzoyl methane (Parsol® 1789) and 2-cyano-3,3-phenylcinnamic acid-2-ethylhexyl ester (Octocrylene), in combination with esters of cinnamic acid, preferably 4-methoxycinnamic acid-2-ethylhexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example µmole to µmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Biogenic Agents

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prune extract, bambara nut extract, and vitamin complexes.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Hydrotropes

In addition, hydrotropes, for example ethanol, isopropyl alcohol or polyols, may be used to improve flow behavior during application. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

aminosugars, for example glucamine;

dialcoholamines, such as diethanolamine or 2-aminopropane-1,3-diol.

Preservatives

Suitable preservatives are, for example, phenoxyethanol, formaldehyde solution, parabens, pentanediol or sorbic acid and the silver complexes known under the name of Surfacine® and the other classes of compounds listed in Appendix 6, Parts A and B of the Kosmetikverordnung ("Cosmetics Directive").

Perfume Oils

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemi, W Inhelm, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular composition. The compositions may be produced by standard hot or cold processes.

EXAMPLES

Various impregnating solutions were prepared simply by mixing the components. Thin cotton gloves weighing 12 g were then wetted with 20 g of surfactant solution 3 or 4 and rubbed into hair in the form of short or shoulder-length hair. The treated hair showed a distinct cleaning effect in increased volume, a lower fat content and a pleasant luster.

In a second test, the gloves impregnated with surfactant solutions 3 and 4 were dried for 24 hours at 30° C. Before use, the dry impregnated gloves were rewetted with 18 g water. The hair thus treated showed the same effect, albeit to a somewhat lesser extent.

TABLE 1

Composition of the impregnating solution concentrates
Quantities in % by weight

| Composition | 1 | 2 |
|---|---|---|
| $C_{12-14}$ cocoalcohol + 5EO + 4PO | 10.0 | — |
| Dehypon Ke 3447 (HME)[1] | — | 11.1 |
| $C_{8-10}$ alkyl oligoglucoside | 63.0 | 63.0 |
| Bronidox[2] | 0.3 | 0.3 |
| Citric acid | 2.5 | 2.5 |

TABLE 1-continued

Composition of the impregnating solution concentrates
Quantities in % by weight

| Composition | 1 | 2 |
|---|---|---|
| Water | to 100 | to 100 |

[1] $C_{8-10}$ fatty alcohol ethylene oxide/propylene oxide 22/1 + decene epoxide
[2] Propylene Glycol (and) 5-Bromo-5-Nitro-1,3-Dioxane

TABLE 2

Composition of the impregnating solutions
Quantities in % by weight

| Composition | 3 | 4 |
|---|---|---|
| Surfactant solution concentrate 1 | 4.0 | — |
| Surfactant solution concentrate 2 | — | 3.8 |
| Perfume oil | 0.2 | 0.2 |
| Preservative | 0.1 | 0.1 |
| Ethanol | 8.0 | 8.2 |
| Water | to 100.0 | to 100 |
| pH value | 5.5 | 5.5 |

What is claimed is:

1. A cleaning cloth comprising: (a) a fibrous web; (b) an alkyl or alkenyl oligoglycoside; and (c) a member selected from the group consisting of an alcohol polyglycol ether, a hydroxy mixed ether, or a combination thereof.

2. The composition of claim 1 wherein the amount of component (b) is from 0.05 to 2% by weight.

3. The composition of claim 1 wherein the amount of component (c) is from 0.01 to 1% by weight.

4. The composition of claim 1 further comprising a cleaning solution.

5. The composition of claim 4 wherein the weight ratio of the dry cloth to the cleaning solution is from 1:0.1 to 1:4.

6. The composition of claim 1 further comprising from 10 to 70% by weight of water based on the weight of the wet cleaning cloth.

7. The composition of claim 1 wherein the fibrous web is a cotton fabric or a cotton blend fabric.

8. The composition of claim 1 wherein the fibrous web is a hydrophilic polyolefin fabric.

9. The composition of claim 7 wherein the fibrous web is a cotton fabric or a cotton blend fabric in the form of a glove.

10. A process for producing a cleaning cloth comprising contacting a fibrous web with a solution comprised of: (a) solvent; (b) an aqueous surfactant solution comprised of (i) an alkyl or alkenyl oligoglycoside; and (ii) a member selected from the group consisting of an alcohol polyglycol ether, a hydroxy mixed ether, or a combination thereof.

11. A process for producing a cleaning cloth comprising the steps of: (1) contacting a fibrous web with a solution comprised of: (a) solvent; (b) an aqueous surfactant solution comprised of (i) an alkyl or alkenyl oligoglycoside; and (ii) a member selected from the group consisting of an alcohol polyglycol ether, a hydroxy mixed ether, or a combination thereof to form a wet fibrous web; (2) drying the wet web to reduce the solvent content to from 0.1% to 3% by weight of the cleaning cloth.

* * * * *